United States Patent
Harwood

(10) Patent No.: US 6,239,874 B1
(45) Date of Patent: May 29, 2001

(54) ORIENTATION DETECTOR ARRANGEMENT

(75) Inventor: Adrian Douglas Harwood, High Wycombe (GB)

(73) Assignee: Armstrong Healthcare Limited, Buckinghamshire (GB)

( * ) Notice: Subject to any disclaimer, the term of this patent is extended or adjusted under 35 U.S.C. 154(b) by 0 days.

(21) Appl. No.: 09/308,093

(22) PCT Filed: Oct. 21, 1997

(86) PCT No.: PCT/GB97/02910

§ 371 Date: Jul. 7, 1999

§ 102(e) Date: Jul. 7, 1999

(87) PCT Pub. No.: WO98/22832

PCT Pub. Date: May 28, 1998

(30) Foreign Application Priority Data

Nov. 18, 1996  (GB) .................................... 9623911

(51) Int. Cl.[7] .................................................. G01B 11/14
(52) U.S. Cl. .............................................. 356/375; 356/385
(58) Field of Search .................................... 356/375, 385, 356/152.1, 152.2, 152.3, 141.1, 141.2, 141.3, 153, 154; 340/825.7; 250/216, 203.3, 203.5

(56) References Cited

U.S. PATENT DOCUMENTS

| | | | |
|---|---|---|---|
| 3,678,283 | * 7/1972 | LaBaw | 250/216 |
| 4,067,015 | * 1/1978 | Mogavero et al. | 340/825.7 |
| 4,175,861 | * 11/1979 | Kottas | 356/153 |
| 4,475,814 | * 10/1984 | Marche | 356/375 |
| 5,179,421 | * 1/1993 | Parker et al. | 356/152.1 |
| 5,296,854 | 3/1994 | Hamilton et al. | |
| 5,622,170 | * 4/1997 | Schulz | 356/375 |
| 5,657,128 | * 8/1997 | Muller et al. | 356/375 |
| 5,987,349 | * 11/1999 | Schulz | 356/375 |

FOREIGN PATENT DOCUMENTS

| | | |
|---|---|---|
| 2284957 | 6/1995 | (GB) . |
| 95/19577 | 7/1995 | (WO) . |
| 96/35960 | 11/1996 | (WO) . |

* cited by examiner

Primary Examiner—Frank G. Font
Assistant Examiner—Sang H. Nguyen
(74) Attorney, Agent, or Firm—Harrison & Egbert

(57) ABSTRACT

An orientation detector arrangement is adapted to detect the orientation of a first component relative to a second component, preferably during endoscopic surgery. The first component is a transmitter which may be worn on a surgeon's head. The transmitter is adapted to transmit a plurality of unique identifiable signals along mutually diverging beams. The second component is a detector which is adapted to distinguish between the individual signals transmitted by the transmitter. The detector is connected by a control circuit to an endoscopic camera which is, in turn, connected to provide an image on a display screen. The detector and the associated control circuit are able to control movement of the endoscopic camera in response to movement of the surgeon's head.

10 Claims, 1 Drawing Sheet

ORIENTATION DETECTOR ARRANGEMENT

TECHNICAL FIELD

THE PRESENT INVENTION relates to an orientation detector, arrangement, and in particular relates to an orientation detector arrangement adapted to detect the orientation of one component relative to another component.

The invention will be described with reference to a specific embodiment, which has been devised for use where a particular need exists, but the invention may find other applications.

BACKGROUND ART

In certain surgical situations, for example in endoscopic surgery, the surgeon requires to use both hands simultaneously to manipulate various instruments, but also requires to control the position of the endoscopic camera. The present invention seeks to provide an arrangement that may be used by a surgeon to control an item such as a camera without moving his hands or feet.

WO96/35960 discloses a complex system for determining the position and orientation of a movable object in space relative to a stationary object in which two transmitter units are mounted in a fixed spaced relationship on a stationary consul, and two receiver units are mounted on the movable object which may, for example, be a head-set. Each transmitter unit has a triplet of orthogonally arranged light-emitting diodes, each of which generates a hemispherical beam of radiation. The beams of radiation substantially overlap. Each receiver unit has six photo-detectors, each of which has a plane of sensitivity such that the intensity of incidence radiation is proportional to the co-sign of the angle of incidence of the radiation. The six photo-detectors are arranged so that they form four sets of three photo-detectors with the photo-detectors in each set having their planes of sensitivity arranged orthogonally. Each of the photo-detectors generates a direction co-sign signal proportional to the intensity of radiation received from each LED.

The described arrangement is relatively complex, and relies on each photo-detector receiving light from a substantial number of the light-emitting diodes. The arrangement does generate a control signal, which depends upon the ratio of the intensities of the radiation received by each photo-detector from each light-emitting diode.

GB 2,284,957A discloses an optical system for the remote tracking of the position and/or orientation of an object such as the helmet of a pilot. The Specification teaches that two groups of light-emitting diodes are provided on the helmet, and light from the light-emitting diodes are imaged on to photo-sensitive layers of two position sensitive detectors. An output signal is provided from each layer which depends upon the position of the spots of light imaged on to the layer from the light-emitting diodes. The output signals is used to track movement of the helmet of the pilot.

SUMMARY OF THE INVENTION

According to this invention there is provided an orientation detector arrangement, adapted to detect the orientation of a first component relative to a second component, wherein the first component comprises transmitter means adapted to transmit a plurality of diverging beams, each beam being uniquely identifiable, the second component comprising a detector, the detector being adapted to detect and distinguish the beams transmitted by the transmitters, the detector being associated with a control circuit adapted to generate a control signal in dependence upon the identity of a beam or beams detected by the detector.

Conveniently each beam is a beam of light in or near the visible spectrum.

Advantageously each beam is a beam of infra-red light.

In one embodiment each beam is pulse-code modulated in a unique way. In a preferred embodiment each beam carries a signal generated by an oscillator, which oscillates at a unique respective frequency.

Conveniently the means to distinguish the beams is a plurality of tuned circuits, each tuned circuit being tuned to a frequency of a respective one of the oscillators.

Preferably the first component is provided with means to enable the first component to be worn on the head of a person.

Advantageously the first component comprises a housing provided with a head-band or strap.

Conveniently the detector is provided on or adjacent a visual display. Advantageously the control circuit is adapted to control the operation of a component which causes the image on the visual display unit or monitor to alter.

Preferably the control circuit controls a camera, the image from the camera being displayed on the visual display unit or monitor.

Alternatively the control circuit controls a component which is visible in the image as shown on the visual display unit or monitor, or which, when controlled, causes said image to change.

According to another aspect of this invention there is provided a control apparatus comprising a first component adapted to be worn on the head of an operator, the first component having means which emit a plurality of diverging beams, each beam being uniquely identifiable, and detector means to determine the orientation of the first component and control means to generate a control signal in accordance with the orientation of the first component, the detector means being adapted to detect and identify the beam or beams being received, the detector means being associated with the control means which are adapted to generate a control signal in dependence upon the identity of the beam or beams detected, wherein the control means control movement or function of a further device.

Advantageously the further device is a camera, the detector means being located on or adjacent a visual display unit or monitor adapted to display an image of the scene viewed by the camera.

Alternatively the means are located on or adjacent a visual display unit or monitor adapted to display an image of a scene viewed by a camera, the further device comprising a component which is visible within that scene.

BRIEF DESCRIPTION OF THE DRAWINGS

In order that the invention may be more readily understood, and so that further features thereof may be appreciated, the invention will now be described, by way of example, with reference to the accompanying drawings in which.

DETAILED DESCRIPTION OF THE INVENTION

Figure 1:
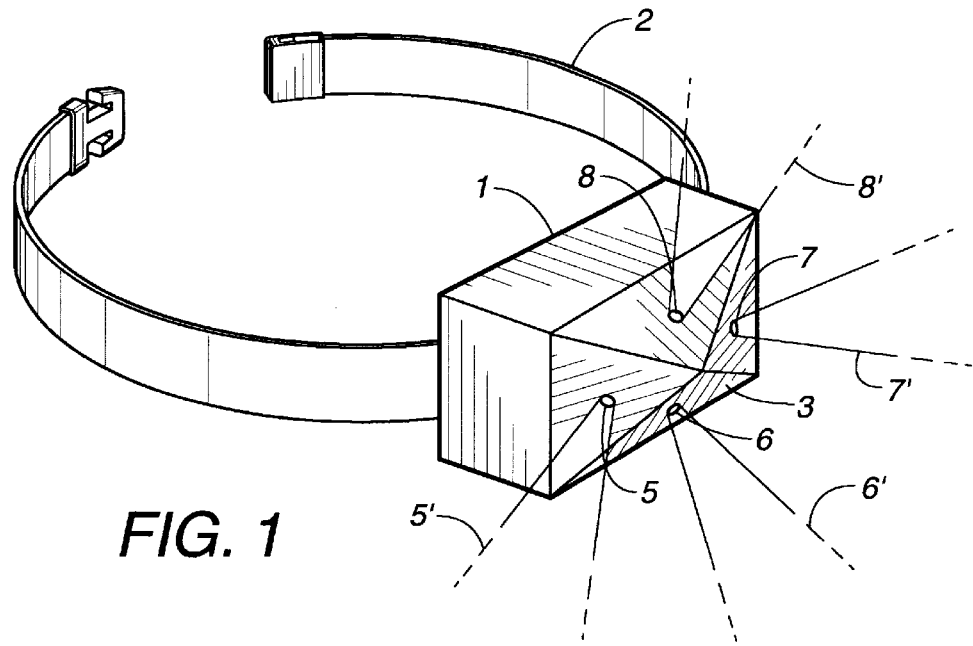
FIG. 1 is a perspective view of a first component in the form of a transmitter adapted to be worn on the head of a person, such as a surgeon.

Referring initially to FIG. 1 of the drawings, a first component comprises a transmitter assembly which includes a housing 1 associated with a band or strap 2, which is provided to enable the housing 1 to be secured to the head of a person, such as a surgeon. It is to be appreciated that the housing may be provided with any appropriate means to retain the housing in position and may be incorporated into an appropriate surgeon's hat.

The front face 3 of the housing is provided with a plurality of transmitters. In the embodiment illustrated four transmitters 5, 6, 7, 8 are provided. The transmitters are adapted to transmit signals, the signals being directed along mutually diverging beams. In the embodiment illustrated, the beams 5', 7' from the transmitters 5 and 7 are located on a substantially horizontal plane but are directed to diverge away from a center line which extends perpendicularly from the housing 1. Similarly, the beams 6', 8' from the transmitters 6 and 8, diverge downwardly and upwardly, respectively, from the center line. The four beams illustrated thus mutually diverge away from each other. The divergence of the beams has been substantially exaggerated in the drawings in order to facilitate an understanding of the invention. In a practical embodiment the beams would be much closer to being parallel than as presently illustrated.

Although, in the presently described embodiment of the invention, four transmitters are provided, it is to be appreciated that any appropriate number of transmitters may be provided to generate the diverging beams.

Each beam 5', 6', 7', 8' will be of generally conical form.

Although the transmitters may transmit radiation of an appropriate frequency it is considered that the optimum form of transmitter comprises a transmitter which transmits light in or near the visible spectrum. The transmitters may comprise light-emitting diodes or lamps, and preferably emit infra-red light.

Each transmitter will be associated with appropriate means to form the respective conical beams discussed above. Thus, each transmitter may be associated with one or more lenses, or one or more shutters or irises.

The signal transmitted by each transmitter is different from the signal transmitted by the other transmitters. Thus, for example, each transmitter may transmit light of a different color or wavelength. Alternatively, each transmitter may transmit light which is pulse-coded in a unique manner. It is preferred, however, that each transmitter is driven by an oscillator of a different frequency. Thus, each beam carries a frequency which is unique to that beam.

It is to be appreciated, therefore, that the illustrated transmitter transmits four diverging beams, each of which is uniquely identifiable.

Figure 2:
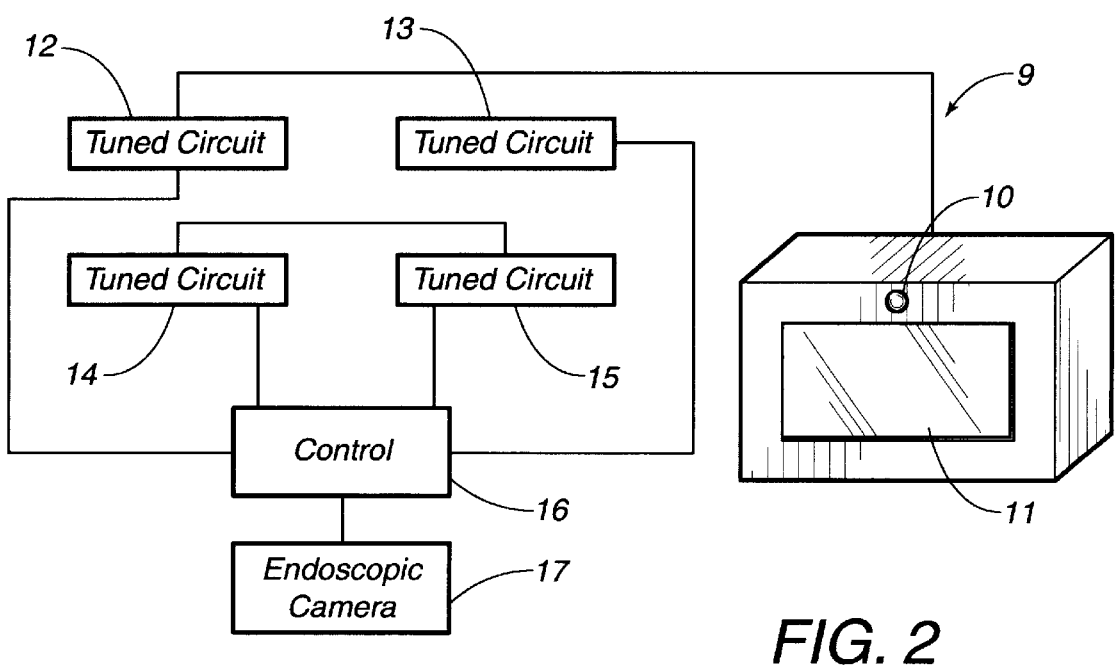
FIG. 2 is a part perspective and part diagrammatic view illustrating a visual display unit or monitor provided with sensors and an associated control arrangement.

FIG. 2 illustrates a visual display unit or monitor 9 provided with a detector 10 located adjacent the screen 11 of the visual display unit or monitor.

The detector 10 is adapted to detect the signal generated by the transmitters.

The detector may be an appropriate photo-sensor which is connected to means adapted to distinguish the signals transmitted from the transmitters. The distinguishing means may comprise filters responsive to the frequencies of the different colors of light transmitted, if this expedient is used, or digital means adapted to distinguish signals with different pulse-codings, if this distinguishing means is used. However, in the preferred embodiment, where the transmitters are driven by oscillators of different frequencies, the detector is associated with four tuned circuits 12, 13, 14, 15, which may comprise phase-locked loops, each tuned circuit being tuned to a respective one of the transmitter frequencies.

In the embodiment illustrated, the tuned circuits are connected to a control circuit 16 which is adapted to control an endoscopic camera 17. The endoscopic camera 17 is connected to provide an image on the screen 11.

It is to be understood that a surgeon using the arrangement described and illustrated will wear the housing 1 on his head in such a position that when the surgeon is looking directly at the screen 11 of the visual display unit or monitor 9, the center line between the diverging beams is aligned with the detector 10. Because the beans diverge, the detector 10 will not receive any signal from any one of the transmitters 5, 6, 7 or 8. Should the surgeon move his head, for example, towards the left, the beam 5' from the transmitter 5 will begin to impinge on the detector 10. The appropriate tuned circuit will generate an output which is fed to the control circuit 16. The control circuit 16 will be adapted to move the endoscopic camera to the left. Thus, by moving his head to the left, the surgeon will be able to control the movement of the camera, so that the camera moves to the left.

It is to be appreciated that should the surgeon move his head towards the right, the beam 7' from the transmitter 7 will be detected by the detector 10 and the appropriate tuned circuit will provide an output to the control circuit 16 causing the endoscopic camera to move to the right. A corresponding effect is experienced if the surgeon should move his head up or down.

If the beams 5', 6', 7', 8' have an appropriate divergence, where the beams reach the detector 10, the beams may, in certain regions, overlap.

In such a situation, should the surgeon move his head so as to observe, for example, the top left-hand corner of the screen, the detector 10 will detect a signal from the transmitter 5 and also from the transmitter 6. The camera 17 may thus be controlled to move leftwardly and upwardly.

It is thus to be appreciated that by moving his head appropriately, the surgeon may provide eight possible control signals to effect movement of the endoscopic camera.

Although the invention has been described, by way of example, as controlling an endoscopic camera, it is to be appreciated that an arrangement similar to that illustrated in FIGS. 1 and 2 may be utilized to control other items, such as a manipulator or a robotic device provided to assist a surgeon. The manipulator may manipulate an item that is visible in the image displayed on the visual display unit or monitor 9.

Whilst the invention has been described, by way of example, with reference to an apparatus intended for use by a surgeon, it is to be appreciated that the embodiments of the invention may find many other uses, especially where people have to perform complicated functions that require the use of both hands and where further control functions need to be carried out. It is envisaged that the invention may find other uses.

Although, in the described embodiment of the invention, the housing containing the transmitters is moved relative to the detector, it is to be appreciated that in alternative embodiments of the invention, the detector may move relative to the housing containing the transmitters. As the detector moves from an initial position in which it is aligned with the center line, the detector will receive the signal transmitted by one or more of the transmitters. An appropriate control function can then be performed, Such an embodiment is, of course, still relying on the fact that the orientation of the transmitter housing relative to the receiver is being detected.

What is claimed is:

1. An orientation detector apparatus comprising:

a movable component having a transmitter means affixed thereto, said transmitter means for transmitting a plurality of diverging beams, each of said diverging beams having a distinguishing identity from the other diverging beams of said plurality of diverging beams;

a fixed component having a detector means thereon, said detector means for detecting and distinguishing said plurality of diverging beams transmitted by said transmitter means; and a control circuit means interactive with said detector means, said control circuit means for generating a control signal in dependence upon an individual identity of the beam detected by said detector means, said movable component being orientable relative to said fixed component.

2. The apparatus according to claim 1 wherein each beam of said plurality of diverging beams is a light signal which carries a signal generated by an oscillator, said light signal oscillating at a frequency different than a frequency of the respective signal of the other diverging beams.

3. The apparatus according to claim 2 wherein said detector means is connected to a plurality of tuned circuits, each of said plurality of tuned circuits being tuned to a frequency of a respective oscillator.

4. The apparatus according to claim 1 wherein the movable component is affixed to a support means, said support means for enabling said movable component to be worn on a head of person.

5. The apparatus according to claim 1 wherein the detector means is connected to a visual display unit, the apparatus further comprising:

a camera connected to said control circuit means, said control circuit means for controlling said camera such that an image from said camera is displayed on the visual display unit.

6. The apparatus according to claim 1, further comprising:

a visual display unit connected to said control circuit means, said detector means is connected to said visual display unit, said control circuit means for controlling an operation of a component which is visible in an image shown on said display unit.

7. A control apparatus comprising;

a first component having means for wearing said first component on a head of an operator, said first component having means for emitting a plurality of diverging beams, each of said diverging beams having a distinguishing identity from the other diverging beams of said plurality of diverging beams;

detector means for determining an orientation of said first component, said detector means being in a fixed position relative to said first component; and control means for generating a control signal relative to an orientation of said first component with respect to said detector means, said detector means for detecting and identifying a beam being received from said plurality of diverging beams, said detector means being connected to said control means, said control means for generating a control signal relative to an individual identity of the beam detected by said detector means, said control means for controlling a movement or function of an external device.

8. The apparatus according to claim 7 wherein said external device is a camera, said detector means being located on or adjacent to a visual display unit, said control means for displaying an image of a scene viewed by said camera.

9. The apparatus according to claim 7 wherein said detector means are located on or adjacent to a visual display unit, said control means for displaying an image of a scene viewed by a camera, the external device comprising a component which is visible within said scene.

10. A control apparatus for controlling an image on a visual display unit, the control apparatus comprising:

a first component having means for enabling said first component to be secured to a head of a person, said first component having four transmitters each of which emits a beam of light which diverges from the other beams of light from said four transmitters, each beam of light having an identity distinguishable from the other beams of light;

a fixed visual display means for displaying an image from a camera;

a detector means interactive with said fixed visual display means, said detector means for detecting and distinguishing the beams of light; and a control means interactive with said detector means for generating a control signal relative to the identity of an individual beam being detected, said control means for controlling said camera so that a movement in one direction of the head of the person wearing said first component causes said camera to move in a corresponding direction.

* * * * *